(12) United States Patent
Hüglin et al.

(10) Patent No.: US 7,700,078 B2
(45) Date of Patent: Apr. 20, 2010

(54) STABILIZATION OF BODY-CARE AND HOUSEHOLD PRODUCTS

(75) Inventors: Dietmar Hüglin, Eimeldingen (DE); Thomas Ehlis, Freiburg (DE); Erich Kramer, Basel (CH); Joseph Anthony Lupia, Colfax, NC (US); Oliver Reich, Grenzach-Wyhlen (DE)

(73) Assignee: Ciba Specialty Chemicals Corporation, Tarrytown, NY (US)

( * ) Notice: Subject to any disclaimer, the term of this patent is extended or adjusted under 35 U.S.C. 154(b) by 0 days.

(21) Appl. No.: 11/133,532

(22) Filed: May 20, 2005

(65) Prior Publication Data

US 2005/0214233 A1    Sep. 29, 2005

Related U.S. Application Data

(63) Continuation of application No. 09/830,788, filed as application No. PCT/EP99/07980 on Oct. 21, 1999, now Pat. No. 6,908,608.

(60) Provisional application No. 60/106,633, filed on Nov. 2, 1998.

(51) Int. Cl.
- *A61K 8/00* (2006.01)
- *A61Q 1/00* (2006.01)
- *A61Q 3/00* (2006.01)
- *A61Q 5/02* (2006.01)
- *A61Q 11/00* (2006.01)
- *A61Q 15/00* (2006.01)

(52) U.S. Cl. .............. 424/59; 424/60; 424/61; 424/62; 424/63; 424/64; 424/65; 424/69; 424/70.1; 424/70.6; 424/70.7; 424/70.9

(58) Field of Classification Search ............ 424/59–65, 424/69, 70.1, 70.6, 70.7, 70.9
See application file for complete search history.

(56) References Cited

U.S. PATENT DOCUMENTS

| | | | | |
|---|---|---|---|---|
| 3,983,132 A | * | 9/1976 | Strobel | 548/260 |
| 4,061,730 A | * | 12/1977 | Kalopissis et al. | 424/47 |
| 4,165,336 A | * | 8/1979 | Bouillon et al. | 562/46 |
| 4,617,374 A | * | 10/1986 | Pruett et al. | 528/288 |
| 5,142,059 A | | 8/1992 | Burdeska et al. | 548/260 |
| 5,688,995 A | | 11/1997 | Luther et al. | 562/30 |
| 5,760,111 A | | 6/1998 | Rembold et al. | 524/100 |
| 6,090,370 A | * | 7/2000 | Luther et al. | 424/59 |

FOREIGN PATENT DOCUMENTS

| | | | |
|---|---|---|---|
| FR | 2194442 | | 3/1974 |
| GB | 2286774 | * | 8/1995 |
| JP | 63-162798 | * | 7/1988 |
| WO | 96/28431 | | 9/1996 |

* cited by examiner

*Primary Examiner*—Barbara P Badio
(74) *Attorney, Agent, or Firm*—Shiela A. Loggins

(57) ABSTRACT

A description is given of the use of light stabilizers of formulae (1) and/or (2) for protecting body-care and household products from photolytic degradation.

2 Claims, No Drawings

STABILIZATION OF BODY-CARE AND HOUSEHOLD PRODUCTS

This application is a continuation of application Ser. No. 09/830,788, now U.S. Pat. No. 6,908,608, filed Jul. 25, 2001, which is the National Stage of International Application PCT/EP99/07980, filed Oct. 21, 1999, which claims the benefit of Provisional Application No. 60/106,633, filed Nov. 2, 1998.

The present invention relates to the use of selected light stabilizers for protecting body-care and household products from photolytic degradation.

The growing product trend of recent years has been to increasingly use transparent (glass) containers for cosmetic formulations and household products. Although both glass and ordinary plastics have a certain inherent absorption in the UV-B-range, the absorption in the UV-A range is very low.

As a consequence, the products change in the course of time through photolytic processes.

This results, for example, in a reduction in viscosity and changes in color or smell.

The object of this invention is to provide additives for body-care and household products which prevent photolytic degradation.

Surprisingly, it has been found that specific light stabilizers based on benzotriazole and triazine meet these requirements.

Accordingly, this invention relates to the use of benzotriazoles of formula

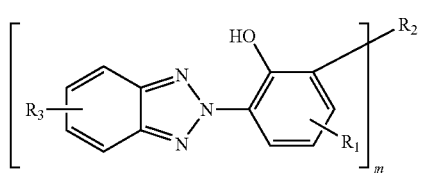
(1)

and/or triazine compounds of formula

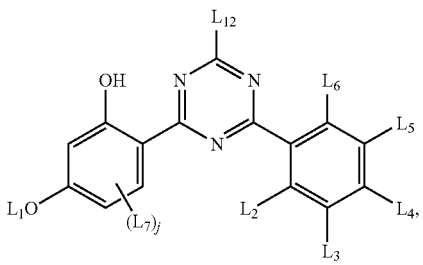
(2)

wherein
R$_1$ is C$_1$-C$_{12}$alkyl; C$_1$-C$_5$alkoxy; C$_1$-C$_5$alkoxycarbonyl; C$_5$-C$_7$cycloalkyl; C$_6$-C$_{10}$aryl; aralkyl; —SO$_3$M; a radical of formula (1a)

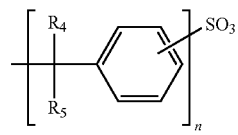

R$_8$ is hydrogen; C$_1$-C5alkyl; C$_1$-C$_5$alkoxy; halogen, preferably Cl; or hydroxy;
R$_4$ and R$_5$ are each independently of the other hydrogen; or C$_1$-C$_5$alkyl;
m is 1 or 2;
n is 0 or 1;
if m=1,
R$_2$ is hydrogen; unsubstituted or phenyl-substituted C$_1$-C$_{12}$alkyl; C$_6$-C$_{10}$aryl;
if m=2,
R$_2$ is a direct bond; —(CH$_2$)$_p$—; and
p is 1 to 3;
L$_1$ is C$_1$-C$_{22}$alkyl, C$_2$-C$_{22}$alkenyl or C$_5$-C$_7$cycloalkly;
L$_2$ and L$_6$ are each independently of the other H, OH, halogen, C$_1$-C$_{22}$alkyl, halomethyl;
L$_3$, L$_5$ and L$_7$ are each independently of one another H, OH, OL$_1$, halogen, C$_1$-C$_{22}$alkyl, halomethyl;
L$_4$ is H, OH, OL$_1$, halogen, C$_1$-C$_{22}$alkyl, phenyl, halomethyl;
L$_{12}$ is C$_1$-C$_{22}$alkyl, phenyl C$_1$-C$_5$alkyl, C$_5$-C$_7$cycloalkyl, OL$_1$ or, preferably, a group of formula j is 0, 1, 2 or 3,
for protecting body-care and household products from photolytic degradation.

C$_1$-C$_{22}$Alkyl is straight-chain or branched alkyl radicals, such as methyl, ethyl, n-propyl, iso-propyl, n-butyl, sec-butyl, tert-butyl, amyl, isoamyl or tert-amyl, heptyl, octyl, isooctyl, nonyl, decyl, undecyl, dodecyl, tetradecyl, pentadecyl, hexadecyl, heptadecyl, octadecyl or eicosyl.

C$_1$-C$_{22}$Alkylthio is straight-chain or branched alkylthio radicals, such as methylthio, ethylthio, n-propylthio, isopropylthio, n-butylthio, sec-butylthio, tert-butylthio, amylthio, heptylthio, octyl-thio, isooctylthio, nonylthio, decylthio, undecylthio, dodecylthio, tetradecylthio, pentadecyl-thio, hexadecylthio, heptadecylthio, octadecylthio or eicosylthio.

$C_2$-$C_{18}$Alkenyl is, for example, allyl, methallyl, isopropenyl, 2-butenyl, 3-butenyl, isobutenyl, n-penta-2,4-dienyl, 3-methyl-but-2-enyl, n-oct-2-enyl, n-dodec-2-enyl, isododecenyl, n-dodec-2-enyl or n-octadec-4-enyl.

$C_5$-$C_7$Cycloalkyl is cyclopentyl, cycloheptyl or, preferably, cyclohexyl.

$C_7$-$C_9$Phenylalkyl is phenylpropyl, phenylethyl and, preferably, benzyl.

If L-substituents are defined as alkyl or alkenyl, or if they are aromatic or aliphatic ring systems, then these contain within the scope of the given meanings usually 1 to 50 carbon atoms and can be interrupted once or several times by O, S, NR', $SO_2$, CO, phenylene, cyclohexylene, COO, OCO, —($SiR_pR_qO$)— and/or substituted once or several times by OH, OR', NR'R'', halogen, —CN, alkenyl, phenyl, —$SiR_pR_qR_r$ or COOH, where R' and R'' are each independently of the other H, alkyl, alkenyl or acyl, and $R_p$, $R_q$ and $R_r$ are each independently of the other H, alkyl, alkenyl, phenyl, alkoxy, acyl or acyloxy.

The above groups can also carry further substituents. Dimers or polymers are also possible.

Preferred 2-hydroxyphenyltriazines of this class are, for example, those of formulae

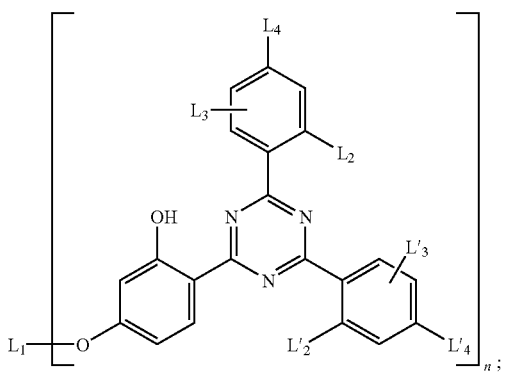

(3)

wherein n is 1 or 2, and $L_1$, where n=1, is $C_1$-$C_{22}$alkyl or $C_1$-$C_{22}$alkyl which is interrupted by one or several O and/or substituted by one or several of the radicals OH, glycidyloxy, $C_2$-$C_{22}$alkenoxy, COOH, $COOR^6$, O—CO—$R^f$; or $C_2$-$C_{22}$alkenyl, $C_5$-$C_7$cycloalkyl; phenylalkyl which is unsubstituted or substituted by OH, Cl or $CH_3$; $COR^g$; $SO_2$—$R^h$; $CH_2CH(OH)$—$R^j$; wherein $R^6$ is $C_1$-$C_{22}$alkyl; $C_2$-$C_{22}$alkenyl; $C_1$-$C_{22}$hydroxyalkyl; $C_1$-$C_{22}$alkyl or $C_1$-$C_{22}$hydroxyalkyl which is interrupted by one or several O; $C_5$-$C_7$cycloalkyl; benzyl; $C_1$-$C_5$alkylphenyl; phenyl; phenyl-$C_1$-$C_5$alkyl; furfuryl; or $CH_2CH(OH)$—$R^j$;

$R^f$, $R^g$ are each independently of the other $C_1$-$C_{22}$alkyl, $C_2$-$C_{22}$alkenyl or phenyl;

$R^h$ is $C_1$-$C_{22}$alkyl, aryl or alkylaryl;

$R^j$ is aralkyl or $CH_2OR^k$;

$R^k$ is $C_5$-$C_7$cyclohexyl, phenyl, tolyl, or benzyl; and $L_1$, where n=2, is alkylene; alkenylene; xylylene; alkylene or hydroxyalkylene which is interrupted by one or several —O—; hydroxyalkylene;

$L_2$ and $L'_2$ are each independently of the other H, $C_1$-$C_{22}$alkyl or OH;

$L_4$ and $L'_4$ are each independently of the other H, alkyl, OH, alkoxy, halogen and, where n=1, $OL_1$;

$L_3$ and $L'_3$ are each independently of the other H, $C_1$-$C_{22}$alkyl or halogen.

$L_1$, $L_2$, $L'_2$, $L_3$, $L'_3$, $L_4$, $L'_4$ can within the scope of the cited meanings carry additional substituents, for example an ethylenically unsaturated polymerisable group. Dimers or polymers are also possible.

Very particularly preferred triazine compounds are those of formula

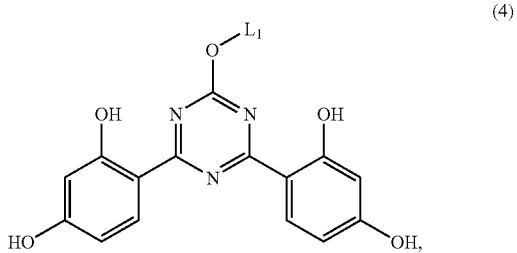

(4)

wherein $L_1$ is $C_2$-$C_{30}$alkyl; $C_2$-$C_{30}$alkenyl; $C_5$-$C_{12}$cycloalkyl, $C_1$-$C_5$alkoxy-$C_1$-$C_{12}$alkyl which is unsubstituted or substituted by one or several $C_1$-$C_5$alkyl; amino-$C_1$-$C_{12}$alkyl; $C_1$-$C_5$monoalkyl-amino-$C_1$-$C_{12}$alkyl; $C_1$-$C_5$dialkylamino-$C_1$-$C_{12}$alkyl.

Examples of such compounds are, inter alia, 2,4,6-tris(2-hydroxy-4-octyloxyphenyl)-1,3,5-triazine, 2-(2,4-dihydroxyphenyl)-4,6-bis(2,4-dimethylphenyl)-1,3,5-triazine, 2,4-bis(2-hydroxy-4-propyloxyphenyl)-6-(2,4-dimethylphenyl)-1,3,5-triazine, 2-(2-hydroxy-4-octyloxyphenyl)-4,6-bis(4-methylphenyl)-1,3,5-triazine, 2-(2-hydroxy-4-dodecyloxyphenyl)-4,6-bis(2,4-dimethylphenyl)-1,3,5-triazine, 2-[2-hydroxy-4-(2-hydroxy-3-butyloxypropyloxy)phenyl]-4,6-bis(2,4-dimethylphenyl)-1,3,5-triazine, 2-[2-hydroxy-4-(2-hydroxy-3-octyloxypropyloxy)phenyl]-4,6-bis(2,4-dimethylphenyl)-1,3,5-triazine, 2-[2-hydroxy-4-(2-hydroxy-3-tridecyloxypropyloxy)phenyl]-4,6-bis(2,4-dimethylphenyl)-1,3,5-triazine; and compounds of the following formulae:

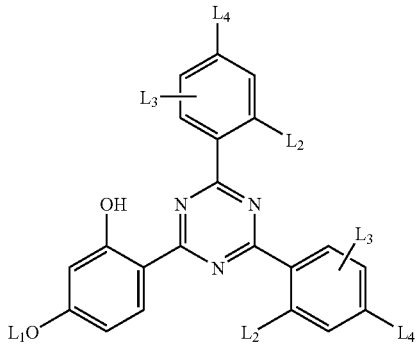

| compound of formula | $L_1$ | L | $L_4$ | L |
|---|---|---|---|---|
| (5) | $CH_2CH(OH)CH_2O-CO-O(CH_3)=CH_2$ | $CH_3$ | $CH_3$ | H |
| (6) | $CH_2CH(OH)CH_2OC_{12}H_{25}/C_{13}H_{27}$(mixture) | $CH_3$ | $CH_3$ | H |
| (7) | $CH_2CH(OH)CH_2O-C_4H_9(n)$ | $CH_3$ | $CH_3$ | H |
| (8) | $CH_2COO-C_{18}H_{37}$ | H | H | m-$CF_3$ |
| (9) | $C_8H_{17}$ | $CH_3$ | $CH_3$ | H |
| (10) | $CH_2CH(OH)CH(C_2H_5)-C_4H_9(n)$ | $CH_3$ | $CH_3$ | H |
| (11) | H | $CH_3$ | $CH_3$ | H |
| (12) | $CH_2CH_2OH$ | H | H | H |
| (13) | $C_6H_{13}$ | H | H | H |
| (14) | $C_{18}H_{37}$ | $CH_3$ | $CH_3$ | o-$CH_3$ |
| (15) | $CH_2CH(OH)CH_2O-C_4H_9(n)$ | H | H | H |
| (16) | $CH(OH)-C_5H_{11}(n)$ | $CH_3$ | $CH_3$ | o-$CH_3$ |
| (17) | $C_8H_{17}$ | H | Cl | H |
| (18) | $CH(CH_3)-COO-C_2H_5$ | $CH_3$ | $CH_3$ | o-$CH_3$ |
| (19) | $CH_2CH(OCOCH_3)CH(C_2H_5)-C_4H_9(n)$ | H | H | H |
| (20) | $CH_2CH(OH)CH(C_2H_5)-C_4H_9(n)$ | H | H | H |
| (21) | $CH_2CH_2-O-CO-C(CH_3)_3$ | H | H | H |
| (22) | H | H | H | H |
| (23) | $(CH_2)_{10}COO-C_2H_5$ | H | Cl | H |
| (24) | $(CH_2)_5COOH$ | H | H | H |
| (25) | $CH_2CH(C_2H_5)-C_4H_9(n)$ | H | H | H |
| (26) | $CH_2CH(OH)CH_2-O-C_4H_9(n)$ | H | H | t-$C_4H_9$H |
| (27) | $CH_2CH(OH)CH_2-O-C_4H_9(n)$ | H | H | $OCH_3$H |
| (28) | $(CH_2)_3-Si(CH_3)_3$ | H | H | H |
| (29) | cyclohexyl | | | |
| (30) | $CH_2CH(OH)CH_2-O$-2-butyl/2-pentyl (mixture) | | | |
| (31) | $CH_2CH(OH)CH_2-O-C_4H_9(n)$ | | | |
| (32) | $(CH_2)_{10}COO-C_2H_5$ | | | |
| (33) | $C_4H_9$ | | | |
| (34) | $CH_2CH(OH)CH(C_2H_5)-C_4H_9(n)$ | | | |
| (35) | $CH(C_3H_7)_2$ | | | |
| (36) | cyclopentyl | | | |
| (37) | $C(CH_3)_2-COO-C_2H_5$ | | | |
| (38) | $CH(CH_3)-COO-C_2H_5$ | | | |
| (39) | $(CH_2)_5-CH_3$ | | | |
| (40) | $CH_3$ | | $OCH_3$ | |
| (41) | $CH_2CH(OCOCH_3)CH(C_2H_5)-C_4H_9(n)$ | | $OCH_2CH_2OC_2H_5$ | |
| (42) | $CH_2CH_2CH_2-O-CO-C_2H_5$ | | $OCH_3$ | |
| (43) | $CH_2CH(OH)CH_2-O-C_4H_9(n)$ | | $CH_3$ | |
| (44) | $CH_2CH(OH)CH_2-O-C_4H_9(n)$ | | $OCH_3$ | |

(45)

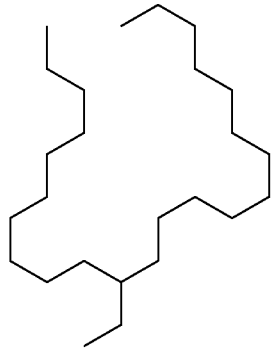

-continued

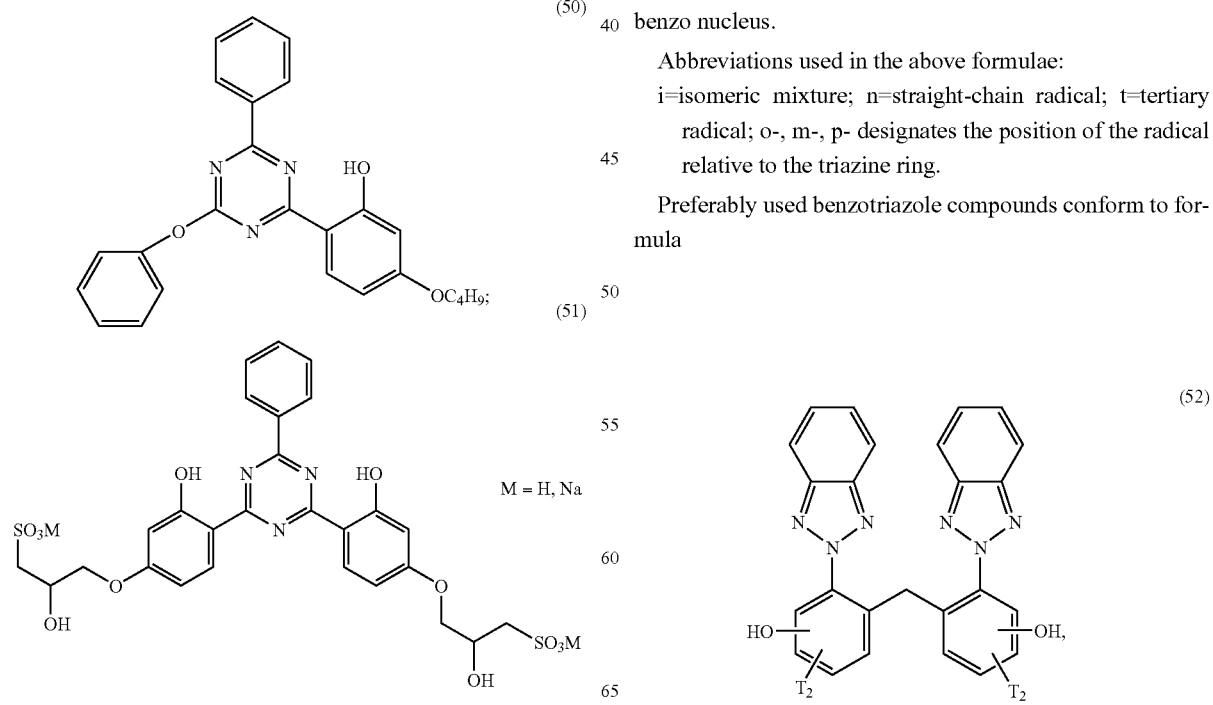

| compound of formula | $L_1$ | $L_3$ | $L_4$ | $L_2$ |
|---|---|---|---|---|
| (46) | iso-$C_8H_{38}$ | | | |
| (47) | | | | |
| (48) | n-$C_{18}H_{37}$ | | | |
| (49) | 2-ethylhexyl | | | | and hydroxyphenyltriazines which are sulfonated in the benzo nucleus.

Abbreviations used in the above formulae:

i=isomeric mixture; n=straight-chain radical; t=tertiary radical; o-, m-, p- designates the position of the radical relative to the triazine ring.

Preferably used benzotriazole compounds conform to formula wherein

T$_2$ is hydrogen or C$_1$-C$_{12}$alkyl.

Examples of benzotriazole compounds used in accordance with this invention:

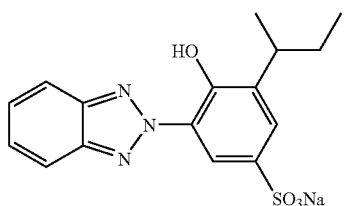
(53)

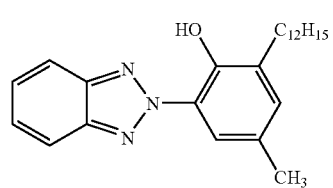
(54)

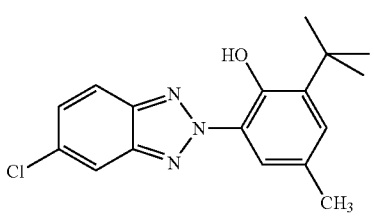
(55)

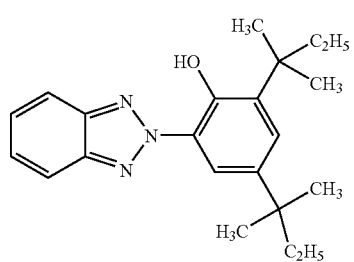
(56)

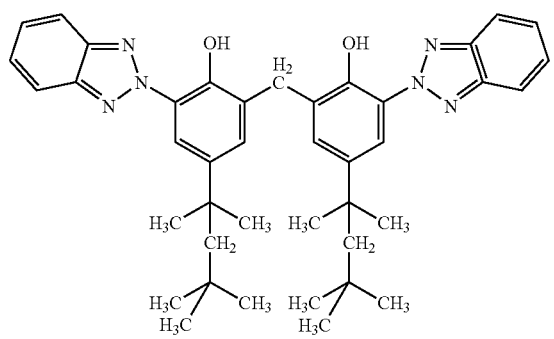
(57)

The light stabilizers of formulae (1) and (2) can also be used together with tocopherol or tocopherol acetate.

The light stabilizers of formulae (1) and (2) can also be used together with sterically hindered amines.

These include preferably a 2,2,6,6-tetraalkylpiperidine derivative containing at least one group of formula

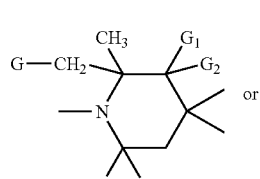
(58)

or

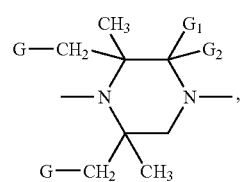
(59)

wherein G, G$_1$ and G$_2$ are each independently of one another hydrogen or methyl, preferably hydrogen.

Examples of tetraalkylpiperidine derivatives which can be used according to this invention are to be found in EP-A-356677, pages 3-17, paragraphs a) to f). The cited paragraphs of this EP-A are regarded as part of the present description. It is particularly useful to employ the following tetraalkylpiperidine derivatives:

bis(2,2,6,6-tetramethylpiperidin-4-yl)sebacate, bis(2,2,6,6-tetramethylpiperidin-4-yl)succinate, bis(1,2,2,6,6-pentamethylpiperidin-4-yl)sebacate, bis(1-octyloxy-2,2,6,6-tetramethyl-piperidin-4-yl)sebacate, n-butyl-3,5-di-tert-butyl-4-hydroxybenzylmalonic acid-bis(1,2,2,6,6-pentamethylpiperidyl)ester, the condensate of 1-hydroxyethyl-2,2,6,6-tetramethyl-4-hydroxy-piperidine and succinic acid, the condensate of N,N'-bis(2,2,6,6-tetramethyl-4-piperidyl)hexamethylenediamine and 4-tert-octylamino-2,6-dichloro-1,3,5-s-triazine, tris(2,2,6,6-tetramethyl-4-piperidyl)nitrilotriacetate, tetrakis(2,2,6,6-tetramethyl-4-piperidyl)-1,2,3,4-butanetetraoate, 1,1'-(1,2-ethanediyl)-bis(3,3,5,5-tetramethylpiperazinone), 4-benzoyl-2,2,6,6-tetramethyl-piperidine, 4-stearyloxy-2,2,6,6-tetramethylpiperidine, bis(1,2,2,6,6-pentamethylpiperidyl)-2-n-butyl-2-(2-hydroxy-3,5-di-tert-butylbenzyl)malonate, 3-n-octyl-7,7,9,9-tetramethyl-1,3,8-triazaspiro[4.5]decane-2,4-dione, bis(1-octyloxy-2,2,6,6-tetramethylpiperidyl)sebacate, bis(1-octyloxy-2,2,6,6-tetramethylpiperidyl)succinate, the condensate of N,N-bis(2,2,6,6-tetramethyl-4-piperidyl)hexamethylenediamine and 4-morpholino-2,6-dichloro-1,3,5-triazine, the condensate of 2-chloro-4,6-di(4-n-butylamino-2,2,6,6-tetramethylpiperidyl)-1,3,5-triazine and 1,2-bis(3-aminopropylamino)ethane, the condensate of 2-chloro-4,6-di(4-n-butylamino-1,2,2,6,6-pentamethylpiperidyl)-1,3,5-triazine and 1,2-bis(3-aminopropylamino)ethane, 8-acetyl-3-dodecyl-7,7,9,9-tetramethyl-1,3,8-triazaspiro[4.5]decane-2,4-dione, 3-dodecyl-1-(2,2,6,6-tetramethyl-4-piperidyl)pyrrolidin-2,5-dione, 3-dodecyl-1-(1,2,2,6,6-pentamethyl-4-piperidyl)-pyrrolidine-2,5-dione, a mixture of 4-hexadecyloxy- and 4-stearyloxy-2,2,6,6-tetramethylpiperidine, the condensate of N,N'-bis(2,2,6,6-tetramethyl-4-piperidyl)hexamethylene-diamine and 4-cyclohexylamino-2,6-dichloro-1,3,5-triazine, the condensate of 1,2-bis(3-aminopropylamino)ethane and 2,4,6-trichloro-1,3,5-triazine and 4-butylamino-2,2,6,6-tetramethylpiperidine (CAS reg. No. [136504-96-6]); (2,2,6,6-tetramethyl-4-piperidyl)-n-dodecyl-succinimide, (1,2,2,6,6-pentamethyl-4-piperidyl)-n-dodecylsuccinimide, 2-undecyl-7,7,9,9-tetramethyl-1-oxa-3,8-diaza-4-oxo-spiro[4,5]decane, the reaction product of 7,7,9,9-tetramethyl-2-cycloundecyl-1-oxa-3,8-diaza-4-oxospiro[4,5]decane and epichlorohydrin, tetra-(2,2,6,6-tetramethylpiperidin-4-yl)-butane-1,2,3,4-tetracarboxylate, tetra(1,2,2,6,6-pentamethylpiperidin-4-yl)-butane-1,2,3,4-tetracarboxylate, 2,2,4,4-tetramethyl-7-oxa-3,20-diaza-21-oxo-dispiro[5.1.11.2]-heneicosan, 8-acetyl-3-dodecyl-1,3,8-triaza-7,7,9,9-tetramethylspiro-[4,5]-decane-2,4-dione, or a compound of formulae

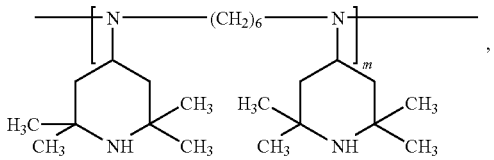 (60)

wherein m is a value from 5-50,

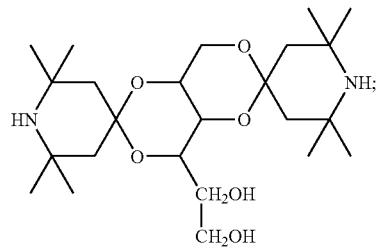 (61)

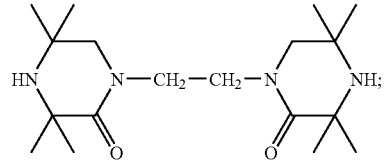 (62)

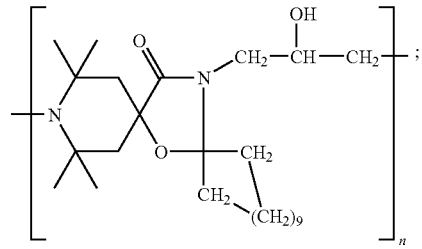 (63)

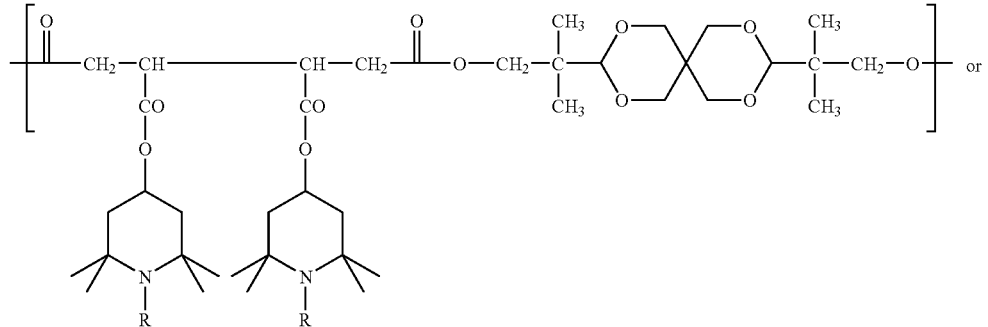 (64)

R = H or CH$_3$

-continued

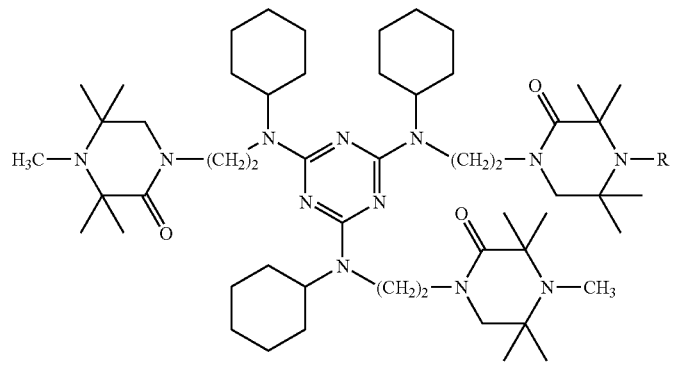

(65)

R = H or CH₃

The light stabilizers of formulae (1) and (2) can furthermore also be used together with complex formers, in particular nitrogen-containing complex formers, for example ethylenediaminetetracetic acid (EDTA), nitrilotriacetic acid (NTA), β-alaninediacetic acid (EDETA) or ethylenediaminedisuccinic acid (EDDS).

Other suitable complex formers conform to formula

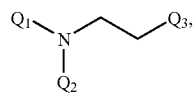
(66)

wherein
- $Q_1$ is $Carb_1$; $Carb_2$; or a radical of formula —$(CH_2)_{m_1}$—OH
- $Q_2$ is hydrogen or $Carb_2$; and
- $Q_3$ is $Carb_3$; an amino acid radical; or a radical of formula (66a)

$Carb_1$, $Carb_2$ and $Carb_3$ being each independently of one another a radical of a $C_1$-$C_8$— mono- or dicarboxylic acid; and
$m_1$ is 1 to 5.

Particularly preferred compounds are those of formula (66), wherein
- $Q_1$ is a monocarboxylic acid; or a radical of formula —$(CH_2)_{m_1}$—OH;
- $Q_2$ is hydrogen or a monocarboxylic acid; and
- $Q_3$ is formula (1b); or a monocarboxylic acid.

Particularly interesting complex formers are those of formula (66), wherein $Carb_2$ and $Carb_3$, are each independently of the other a radical of formula —$[(CH_2)]_{n_1}$—COOH, (66c)

wherein
$n_1$ is 0 to 5.

Complex formers which are important in practice conform to formula

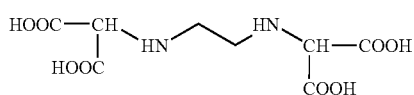
(67)

or to formula

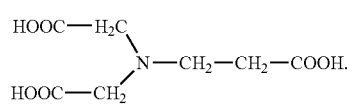
(68)

Nitrilotriacetic acid (NTA) is also suitable for use.

Other examples of inventive complex formers are aminetrimethylenephosphoric acid (ATMP) conforming to formula

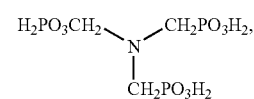
(69)

serinediacetic acid (SDA) conforming to formula

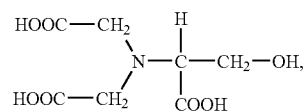
(70)

asparaginediacetic acid conforming to formula

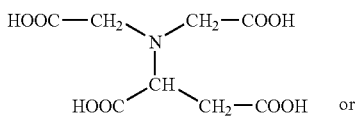 (71)

or methylglycinediacetic acid (MGDA) conforming to formula

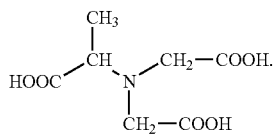 (72)

Other suitable complex formers are polyanionically-derived natural polysaccharides, for example containing phosphate, phosphonate or methylphosphonate groups, such as chitin derivatives, e.g. sulfochitin, carboxymethylchitin, phosphochitin, chitosan derivatives, for example sulfochitosan, carboxymethylchitosan or, very particularly preferably, phosphochitosan, which conform to formula

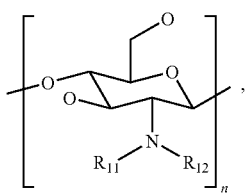 (73)

wherein $R_{11}$ is hydrogen or a radical of formula

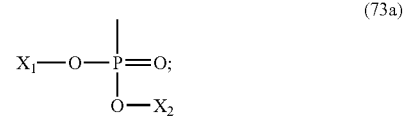 (73a)

$R_{12}$ is a radical of formula (73a);

$X_1$ and $X_2$ are each independently of the other hydrogen, $C_1$-$C_5$alkyl or an alkali ion or ammonium ion; and n is 10 to 4000.

The light stabilizers of formulae (1) and (2) can also be used together with phenolic antioxidants of formula

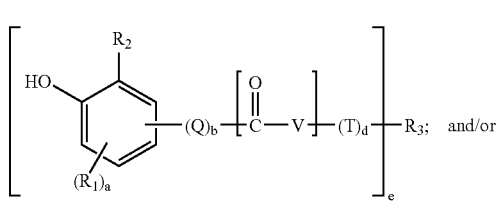 (74)

and/or

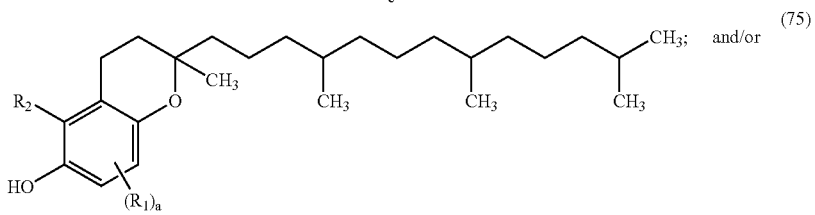 (75)

and/or

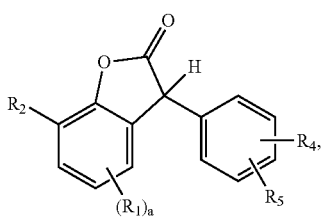 (76)

wherein in formulae (72), (73) and (74)

$R_1$ is hydrogen; $C_1$-$C_{22}$alkyl; $C_1$-$C_{22}$alkylthio; $C_5$-$C_7$cycloalkyl; phenyl; or $C_7$-$C_9$phenylalkyl; or $SO_3M$;

$R_2$ is $C_1$-$C_{22}$alkyl; $C_5$-$C_7$cycloalkyl; phenyl; or $C_7$-$C_9$phenylalkyl;

Q is —$C_mH_{2m}$—;

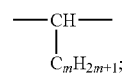

—$C_mH_{2m}$—NH; a radical of formula

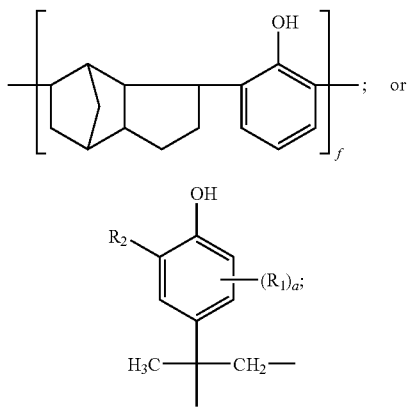
(74a)

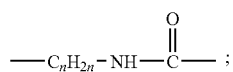
(74b)

T is —$C_nH_{2n}$—; —$(CH_2)_n$—O—$CH_2$—;

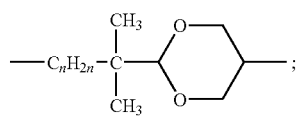

or a radical of formula (74c)

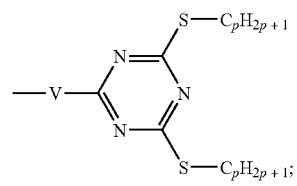

V is —O—; or —NH—;
a is 0; 1; or 2;
b, c and d are each independently of one another 0; or 1;
e is an integer from 1 to 4;
f is an integer from 1 to 3; and
m, n and p are each independently of one another an integer from 1 to 3;
if e=1,
$R_3$ is hydrogen; M; $C_1$-$C_{22}$alkyl; $C_5$-$C_7$cycloalkyl; $C_1$-$C_{22}$alkylthio; $C_2$-$C_{18}$alkenyl; $C_1$-$C_{18}$-phenylalkyl; a radical of formula (74d)

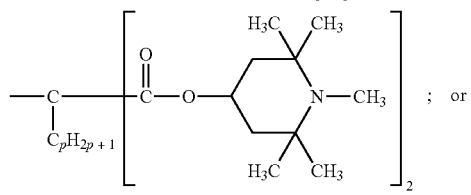

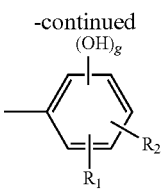

M is alkali; ammonium;
if e=2,
$R_3$ is a direct bond; —$CH_2$—;

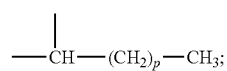

—O—; or —S—;
if
e=3,
$R_3$ is the radical of formula (74g)

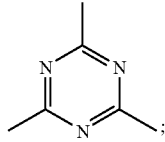
(74g)

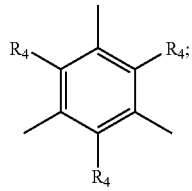
(74h)

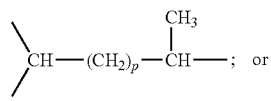
(74i)

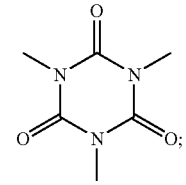
(74k)

if
e=4,
$R_3$ is

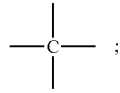

or a direct bond;
$R_4$ and $R_5$ are each independently of the other hydrogen; or $C_1$-$C_{22}$alkyl.

Examples of antioxidants used according to this invention are listed in the following Table:
| compound of formula | |
|---|---|
| (77) | 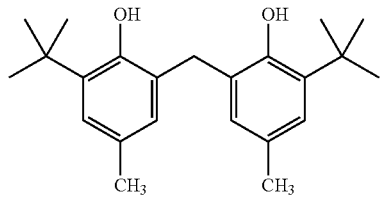 |
| (78) | 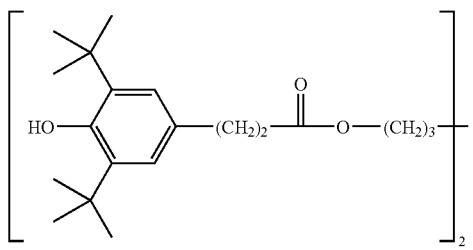 |
| (79) | 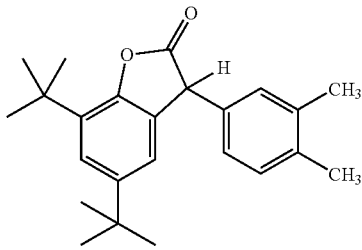 |
| (80) | 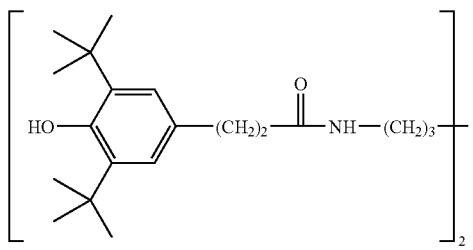 |
| (81) | 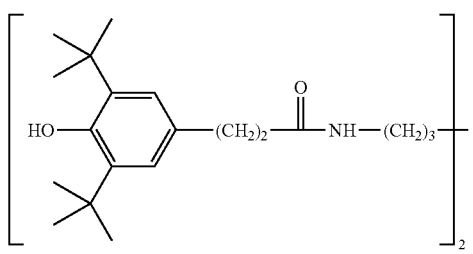 |
| (82) | 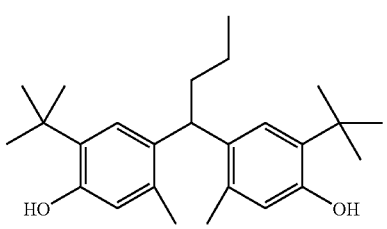 |

-continued
| compound of formula | |
|---|---|
| (83) | 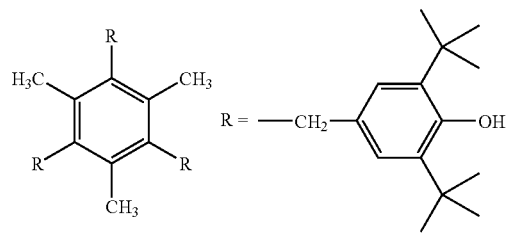 |
| (84) | 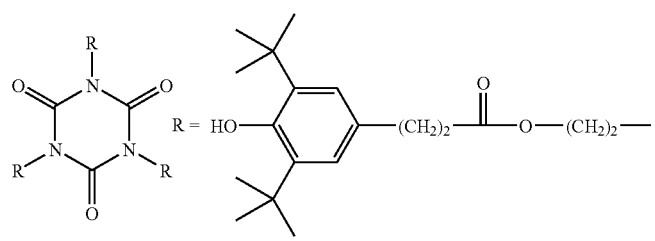 |
| (85) | 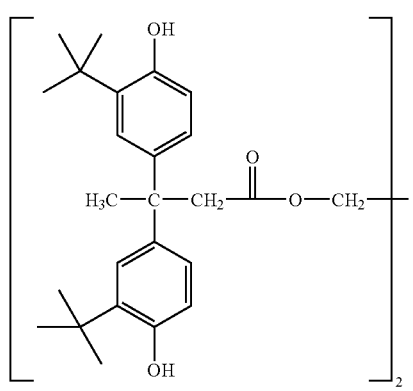 |
| (86) | 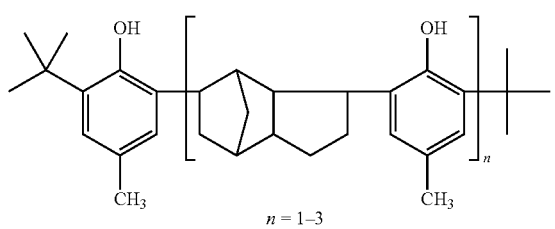 |
| (87) | 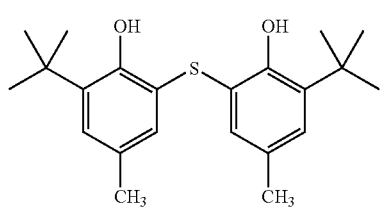 |
| (88) | 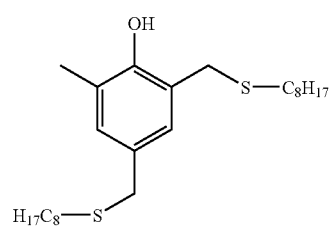 |

-continued
| compound of formula | |
|---|---|
| (89) | 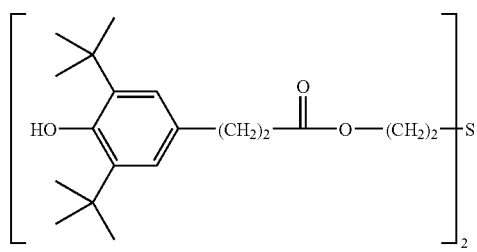 |
| (90) | 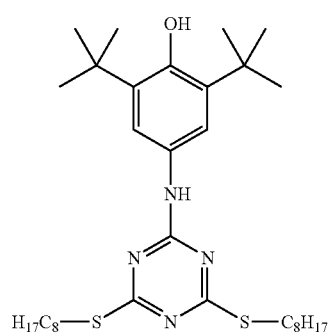 |
| (91) | 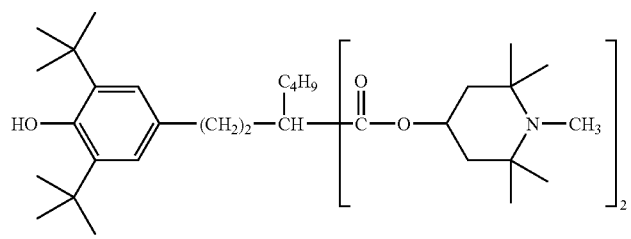 |
| (92) | 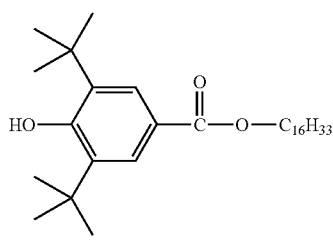 |
| (93) | 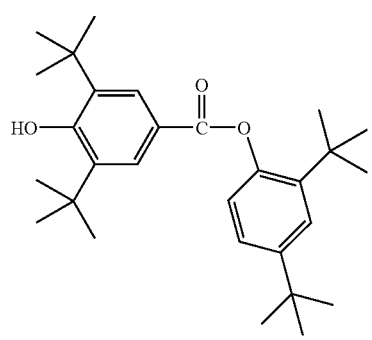 |

-continued
| compound of formula | |
|---|---|
| (94) | 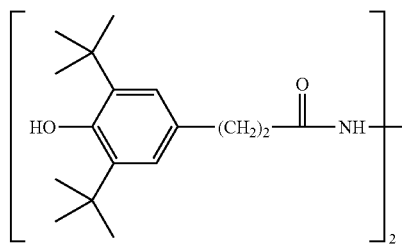 |
| (95) | 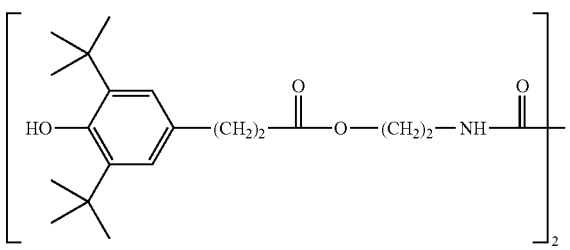 |
| (96) | 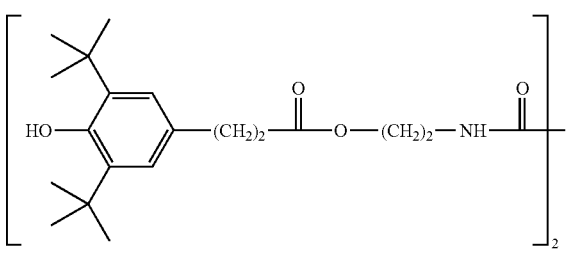 |
| (97) | 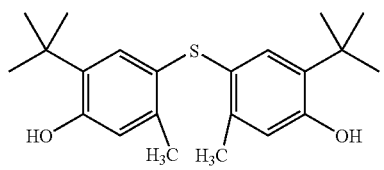 |
| (98) | 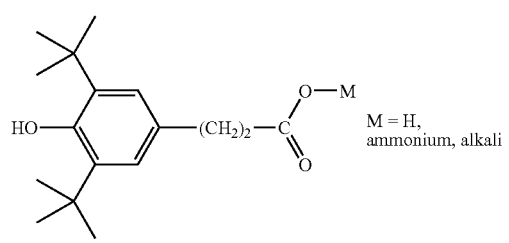 M = H, ammonium, alkali |
| (99) | 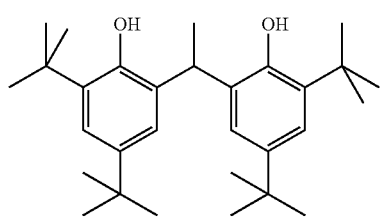 |

| compound of formula | |
|---|---|
| (100) | 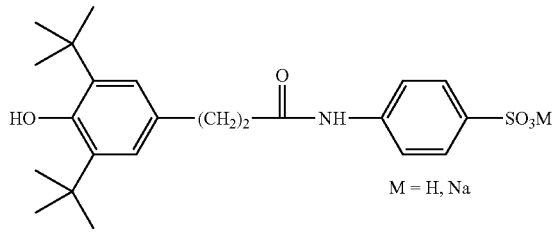 M = H, Na |
| (101) | 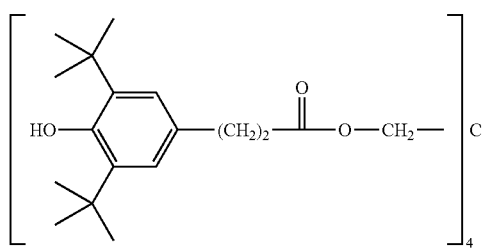 |
| (102) | 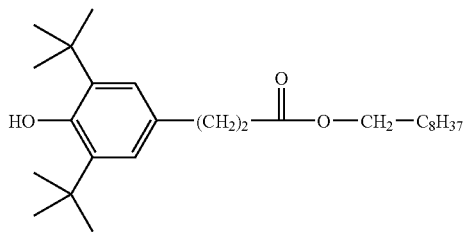 |
| (103) | 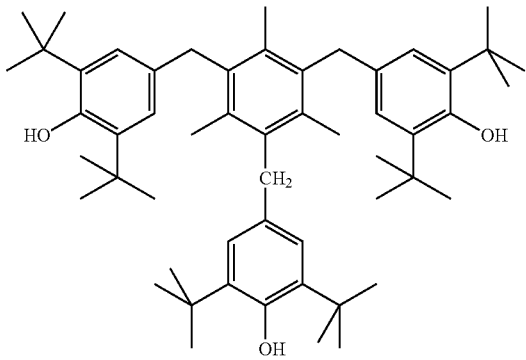 |

The light stabilizers of formulae (1) and (2) as well as mixtures of these compounds with sterically hindered amines, phenolic antioxidants or complex formers are particularly suitable for protecting body-care and household products against photolytic degradation. The compounds or the mixtures of these different compound classes are used in particular in skin-care products, bath and shower additives, preparations containing fragrances and odoriferous substances, hair-care products, dentifrices, deodorizing and antiperspirant preparations, decorative preparations, light protection formulations and preparations containing active ingredients.

Skin-care products are, in particular, body oils, body lotions, body gels, treatment creams, skin protection ointments, shaving preparations, such as shaving foams or gels, skin powders, such as baby powder, moisturizing gels, moisturizing sprays, revitalizing body sprays, cellulite gels and peeling preparations.

Suitable bath and shower additives are shower gels, bath-salts, bubble baths and soaps.

Preparations containing fragrances and odoriferous substances are in particular scents, perfumes, toilet waters and shaving lotions (aftershave preparations).

Suitable hair-care products are, for example, shampoos for humans and animals, in particular dogs, hair conditioners, products for styling and treating hair, perming agents, hair sprays and lacquers, hair gels, hair fixatives and hair dyeing or bleaching agents.

Suitable dentifrices are in particular tooth creams, toothpastes, mouth-washes, mouth rinses, anti-plaque preparations and cleaning agents for dentures.

Suitable decorative preparations are in particular lipsticks, nail varnishes, eye shadows, mascaras, dry and moist make-up, rouge, powders, depilatory agents and suntan lotions.

Suitable cosmetic formulations containing active ingredients are in particular hormone preparations, vitamin preparations, vegetable extract preparations and antibacterial preparations.

The cited body-care products can be in the form of creams, ointments, pastes, foams, gels, lotions, powders, make-ups, sprays, sticks or aerosols. They preferably contain the light stabilizers of formulae (1) and/or (2) and, optionally, sterically hindered amines, complexing agents and phenolic antioxidants in the aqueous phase.

This invention therefore also relates to a body-care product containing at least one light stabilizer of formula (1) and/or (2).

The light stabilizer(s) are usually present in the novel body-care product in a concentration of 50 to 1000 ppm.

Creams are oil-in-water emulsions containing more than 50% of water. The oil-containing base used therein is usually mainly fatty alcohols, for example lauryl, cetyl or stearyl alcohol, fatty acids, for example palmitic or stearic acid, liquid to solid waxes, for example isopropyl-myristate or beeswax and/or hydrocarbon compounds, such as paraffin oil. Suitable emulsifiers are surfactants having primarily hydrophilic properties, such as the corresponding non-ionic emulsifiers, for example fatty acid esters of polyalcohols of ethylene oxide adducts, such as polyglycerol fatty acid ester or polyoxyethylenesorbitan fatty acid ether (Tween trademarks); polyoxyethylene fatty alcohol ether or their esters or the corresponding ionic emulsifiers, such as the alkali metal salts of fatty alcohol sulfonates, sodium cetyl sulfate or sodium stearyl sulfate, which are usually used together with fatty alcohols, such as cetyl alcohol or stearyl alcohol. In addition, creams contain agents which reduce water loss during evaporation, for example polyalcohols, such as glycerol, sorbitol, propylene glycol, and/or polyethylene glycols.

Ointments are water-in-oil emulsions which contain up to 70%, preferably not more than 20 to 50%, of water or of an aqueous phase. The oil-containing phase contains predominantly hydrocarbons, such as paraffin oil and/or solid paraffin which preferably contains hydroxy compounds, for example fatty alcohol or their esters, such as cetyl alcohol or wool wax for improving the water absorption. Emulsifiers are corresponding lipophilic substances, such as sorbitan fatty acid ester. In addition, the ointments contain moisturisers such as polyalcohols, for example glycerol, propylene glycol, sorbitol and/or polyethylene glycol as well as preservatives.

Rich creams are anhydrous formulations and are produced on the basis of hydrocarbon compounds, such as paraffin, natural or partially synthetic fats, for example coconut fatty acid triglycerides or preferably hardened oils and glycerol partial fatty acid esters. Pastes are creams and ointments containing powdered ingredients which absorb secretions, for example metal oxides, such as titanium dioxide or zinc oxide, and also tallow and/or aluminium silicates which bind the moisture or the absorbed secretion.

Foams are liquid oil-in-water emulsions in aerosol form. Hydrocarbon compounds are used, inter alia, for the oil-containing phase, for example paraffin oil, fatty alcohols, such as cetyl alcohol, fatty acid esters, such as isopropylmyristate and/or waxes. Suitable emulsifiers are, inter alia, mixtures of emulsifiers having predominantly hydrophilic properties, for example polyoxyethylenesorbitan fatty acid ester, and also emulsifiers having predominantly lipophilic properties, for example sorbitan fatty acid ester. Commercially available additives are usually additionally employed, for example preservatives.

Gels are, in particular, aqueous solutions or suspensions of active substances in which gel formers are dispersed or swelled, in particular cellulose ethers, such as methyl cellulose, hydroxyethyl cellulose, carboxymethyl cellulose or vegetable hydrocolloids, for example sodium alginate, tragacanth or gum arabic. The gels preferably additionally contain also poly-alcohols, such as propylene glycol or glycerol as moisturizers and wetting agents, such as polyoxyethylenesorbitan fatty acid ester. The gels furthermore contain commercially available preservatives, such as benzyl alcohol, phenethyl alcohol, phenoxyethanol and the like.

Nail-varnishes consist of
- a film forming agent, normally nitro-cellulose;
- a solvent like ethyl acetate, alcohol, toluene, xylene, hexane, heptane, ethyl-isopropyl-, (iso-)butyl- or (iso-)amylacetate, petroleum or ether;
- a resin, like the condensation products of p-toluene sulfonamide and formaldehyde; polyether resins; resins based on polyol dibasic ester; maleic alkyd resins; acrylates; vinyles or polyamid resins.
- plastsizers, for example dibutyl phthalate, camphor, castor oil, acetyltriethyl citrate, di-isobutyl adipate, butyl octyladipate, sucrose acetate-isobutyrate and/or ethyltoluene sulfonamide.
- organic and/or inorganic pigments and/or color varnishes, unusually water soluble dyes;
- light stabilizers, antioxidants and sequestering agents.

Wax-containing basics for lipsticks, make-up or hair-wax consist of
- liquid ingredients like castor oil, oleyl alcohol, Lanolin, PEG, PPG and esters thereof, like isopropyl myristate and/or silicones like dimethyl silicone, unusually also water,
- waxes like bees wax, ozokerit, ceresine, carnauba, candelilla or paraffin waxes.
- organic and/or inorganic pigments and/or color varnishes, also water soluble dyes, for example dyes of the Eosin-type, but also all other water soluble dyes as well as oil soluble dyes;
- dressing for hair/lips or sparkling effect pigments (for example bismuth oxychloride or optical effect pigments);
- perfumes;
- antioxidants, light stabilizers and sequestering agents.

The following Table lists typical examples of body-care products of this invention and their ingredients:

| Body-care product | Ingredients |
| --- | --- |
| moisturizing cream | vegetable oil, emulsifier, thickener, perfume, water, light stabilizer of formula (1) or (2) |
| shampoo | surfactant, emulsifier, preservatives, perfume, light stabilizer of formula (1) or (2) |
| toothpaste | cleaning agent, thickener, sweetener, flavor, colorant, light stabilizer of formula (1) or (2), water |
| lip-care stick | vegetable oil, wax, $TiO_2$, light stabilizer of formula (1) or (2) |

The novel body-care products have high stability towards color changes and photolytic degradation of the ingredients present in these products. This is to be attributed to the effectiveness, color stability, ease of incorporation and hydrolytic stability of the light stabilizers used.

The light stabilizers of formulae (1) and (2) are also used in household cleaning and treating agents, for example in liquid scouring agents, glass detergents, neutral cleaners (all-purpose cleaners), acid household cleaners (bath), WC cleaners, preferably in washing, rinsing and dishwashing agents, clear rinsing agents, dishwasher detergents, shoe polishes, polishing waxes, floor detergents and polishes, metal, glass and ceramic cleaners, textile-care products, agents for removing rust, color and stains (stain remover salt), furniture and multipurpose polishes and leather dressing agents (leather sprays).

Household cleaning agents are aqueous or alcoholic (ethanol or isopropyl alcohol) solutions of one or more of the following components:
  anionic, nonionic, amphoteric and/or cationic surfactants
  soaps, prepared by saponification of animal and vegetable greases
  organic acids, like hydrochloric acid, phosphoric acid, or sulfuric acid,
  for basic products inorganic (NaOH or KOH) or organic bases;
  abrasives for improved cleaning of surfaces,
  waxes and/or silicones for maintenance and protection of surfaces,
  polyphosphates,
  substances which eliminate hypochlorite or halogens;
  peroxides comprising bleaching activators like TAED, for example sodium perborate or $H_2O_2$;
  enzymes;
  in washing detergents discoloration inhibitors, soil-release compounds, grey scale inhibitors, foam inhibitors, fluorescent whitening agents;
  cleaning agents based on wax may comprise solvents selected from benzine, turpentine and/or paraffines and emulsifiers based on wax;
  filling agents like silicates, polyphosphates, Zeolithes for powdery cleaning agents;
  pigments, lakes or soluble dyes;
  perfumes; and
  light stabilizers, antioxidants and chelating agents.

Colored cleaning agents and decorative cosmetic products can comprise the following dyes:
  inorganic pigments, for example iron oxide (Iron Oxide Red, Iron Oxide Yellow, Iron Oxide Black, etc.), Ultramarines, Chromium Oxide Green or Carbon Black;
  natural or synthetic orgnic pigments;
  disperse dyes which may be solubilzed in solvents like direct hair dyes of the HC type, for example HC Red No. 3, HC Blue No. 2 and all other hair dyes listed in International Cosmetic Ingredient Dictionary and Handbook, $7^{th}$ edition 19997) or the dispersion dyes listed in Color Index International or Society of Dyers and Colourists;
  color varnishes (insoluble salts of soluble dyes, like many Ca-, Ba- or Al-salts of anionic dyes);
  soluble anionic or cationic dyes, like acid dyes (anionic), basic dyes (cationic), direct dyes, reactive dyes or solvent dyes.

Generally, for the coloration of household- and body care products all substances are suitable which have an absorption in the visible light of electromagnetic radiation (wave length of ca. 4000 to 700 nm). The absorption is often caused by the following chromophores:
  Azo-(mono-, di, tris-, or poly-)stilbene-, carotenoide-, diarylmethan-, triarylmethan-, xanthen-, acridin-, quinoline, methin- (also polymethin-), thiazol-, indamin-, indophenol-, azin-, oxazin-, thiazin-, anthraquinone-, indigoid-, phtalocyanine- and further synthetic, natural and/or inorganic chromophores.

Typical examples of novel household cleaning and treating agents are:

| Household cleaners/household treating agents | Ingredients |
|---|---|
| detergent concentrate | surfactant mixture, ethanol, light stabilizer of formulae (1) and (2), water |
| shoe polish | wax, wax emulsifier, light stabilizer of formulae (1) and (2), water, preservative |
| wax-containing floor cleaning agent | emulsifier, wax, sodium chloride, light stabiliser of formulae (1) and (2), water, preservative |

The light stabilizers are usually incorporated by dissolution in a liquid formulation component (oil, water, alcohol).

Suitable examples for surfactants used are anionic, nonionic, cationic, zwitterionic and amphoteric synthetic, detersive substances.

Suitable anionic detersive substances are
  sulfates, such as, for example, fatty alcohol sulfates whose alkyl chain has from 8 to 18 carbon atoms, such as, for example, sulfated lauryl alcohol;
  fatty alcohol ether sulfates, such as, for example, the acid esters or salts thereof of a polyadduct of from 2 to 30 mol of ethylene oxide with 1 mol of a $C_8$-$C_{22}$ fatty alcohol;
  the alkali metal salts, ammonium salts or amine salts of $C_8$-$C_{20}$-fatty acids referred to as soaps, such as, for example, coconut fatty acid;
  alkylamidosulfates;
  alkylaminosulfates, such as, for example, monoethanolamine lauryl sulfate;
  alkylamide ether sulfates;
  alkylaryl polyether sulfates;
  monoglyceride sulfates;
  alkanesulfonates whose alkyl chain contains from 8 to 20 carbon atoms, for example dodecylsulfonate;
  alkylamidosulfonates;
  alkylarylsulfonates;
  α-olefinsulfonates;
  sulfosuccinic acid derivatives, such as, for example, alkylsulfosuccinates, alkyl ether sulfosuccinates or alkylsulfosuccinamide derivatives;
  N-(alkylamidoalkyl)amino acids of the formula

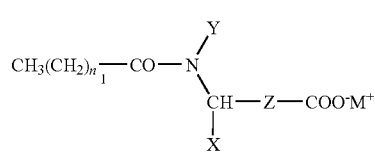

(104)

in which
  X is hydrogen; $C_1$-$C_4$ alkyl or —COOM$^+$;
  Y is hydrogen or $C_1$-$C_4$ alkyl;
  Z is —$(CH_2)_{m1-1}$
  $n_1$ is an integer from 6 to 18 and
  M is an alkali metal cation or ammonium cation;
  alkyl and alkylaryl ether carboxylates of the formula

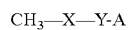

(105)

in which

X is a radical —(CH$_2$)$_{5-19}$—O—;

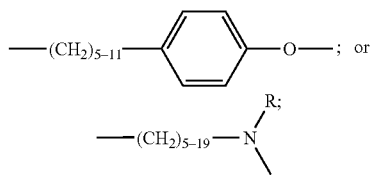

R is hydrogen; or C$_1$-C$_4$ alkyl;
Y is —(CHCHO)$_{1-50}$—;
A is —(CH$_2$)$_{m2-1}$COO$^-$M$^+$; or

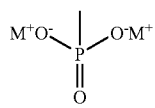

m$_2$ is from 1 to 6 and
M is an alkali metal cation or amine cation.

Other anionic surfactants used are fatty acid methyl taurides, alkylisethionates, fatty acid polypeptide condensates and fatty alcohol phosphoric esters. The alkyl radicals in these compounds preferably have from 8 to 24 carbon atoms.

The anionic surfactants are generally in the form of their water-soluble salts, such as the alkali metal salts, ammonium salts or amine salts. Examples of such salts are lithium, sodium, potassium, ammonium, triethylamine, ethanolamine, diethanolamine or triethanolamine salts. In particular, the sodium, potassium or ammonium (NR$_1$R$_2$R$_3$) salts are used, in which R$_1$, R$_2$ and R$_3$ independently of one another are hydrogen, C$_1$-C$_4$alkyl or C$_1$-C$_4$hydroxyalkyl.

Very particularly preferred anionic surfactants are monoethanolamine lauryl sulfate or the alkali metal salts of fatty alcohol sulfates, in particular sodium lauryl sulfate and the product of the reaction between from 2 to 4 mol of ethylene oxide and sodium lauryl ether sulfate.

Suitable zwitterionic and amphoteric surfactants are C$_8$-C$_{18}$betaines, C$_8$-C$_{18}$sulfobetaines, C$_8$-C$_{24}$alkylamido-C$_1$-C$_4$alkylenebetaines, imidazoline carboxylates, alkylamphocarboxy-carboxylic acids, alkylamphocarboxylic acids (e.g. lauroamphoglycinate) and N-alkyl-β-aminopropionates or -iminodipropionates, the C$_{10}$-C$_{20}$alkylamido-C$_1$-C$_4$ alkylenebetaines and, in particular, coconut fatty acid amidopropylbetaine being preferred.

Examples of nonionic surfactants are derivatives of the adducts of propylene oxide/ethylene oxide having a molecular weight of from 1000 to 15,000, fatty alcohol ethoxylates (1-50 EO), alkylphenol polyglycol ethers (1-50 EO), ethoxylated carbohydrates, fatty acid glycol partial esters, such as, for example, diethylene glycol monostearate, fatty acid alkanolamides and dialkanolamides, fatty acid alkanolamide ethoxylates and fatty amine oxides.

Furthermore, the surfactants may be the salts of saturated and unsaturated C$_8$-C$_{22}$ fatty acids either alone, as a mixture with one another or as a mixture with the other detersive substances mentioned above. Examples of these fatty acids are capric, lauric, myristic, palmitic, stearic, arachidic, behenic, caproleic, dodecenoic, tetradecenoic, octadecenoic, oleic, eicosenoic and erucic acid, and the technical-grade mixtures of such acids, such as, for example, coconut fatty acid. These acids are in the form of salts, suitable cations being alkali metal cations, such as sodium and potassium cations, metal atoms, such as zinc and aluminium atoms, or sufficiently alkaline, nitrogen-containing organic compounds, such as amines or ethoxylated amines. These salts can also be prepared in situ.

Examples for cationic surfactants and conditioning agents which can be used for shampoos and hair conditioners are:

cetyl trimethyl ammonium bromide (CTAB)

dimethicone copolyols amidomethicones acrylamidopropyltrimonium chloride/Acrylamide copolymer guar hydroxypropyl trimonium chloride hydroxycetyl hydroxyethyl dimonium chloride quaternium compounds as listed in International Cosmetic Ingredient Dictionary and Handbook, 7$^{th}$ Edition 1997, for example Quaternium-80.

polyquaternium compounds, as listed in International Cosmetic Ingredient Dictionary and Handbook, 7$^{th}$ Edition 1997, for example polyquaternium-5, polyquaternium-6, polyquaternium-7, polyquaternium-10, polyquaternium-11, polyquaternium-17, polyquaternium-18, polyquaternium-24 or polyquaternium-27, polyquaternium-28, polyquaternium-32, polyquaternium-37.

The surfactant is preferably a soap, i.e. a branched or unbranched long-chain alkyl- or alkenyl-carboxylic acid salt, such as, for example, the sodium, potassium, ammonium or substituted ammonium salt.

The following Examples illustrate the invention.

Preparation of Formulations of Body-Care Products

EXAMPLE 1

Preparation of a Sprayable Hair Styling Gel

| Phase | Ingredients | (w/w) % |
|---|---|---|
| A | carbomer (1% dispersion) | 0.30 |
|   | water, demin. | 30.00 |
| B | glycerol | 2.00 |
|   | methylparaben | 0.20 |
| C | water, demin. | ad 100 |
|   | PVP/VA copolymer | 8.00 |
|   | triethanolamine (88%) | 0.12 |
|   | EDTA, disodium salt | 0.01 |
|   | light stabilizer of formula (53) | 0.01 |

Preparation: The components (A) are dispersed at room temperature. (B) is mixed, with heating, until the paraben is completely dissolved and then (B) is added with gentle stirring to (A). (C) is blended until it is completely dissolved and is slowly added, with stirring, to the mixture of (A) and (B). The transparency of the gel can be increased by adding small amounts of triethanolamine (pH=5.6-5.75).

EXAMPLE 2

Preparation of a Baby Shampoo

| Ingredients | (w/w) % |
| --- | --- |
| cocoamidopropylbetaine | 35.00 |
| water, demin. | ad. 100 |
| citric acid | q.s. (pH) |
| polyquaternium-15 | 0.15 |
| perfume oil | 0.30 |
| chlorophyll | 0.20 |
| light stabilizer of formula (54) | 0.15 |
| antioxidant of formula (102) | 0.05 |
| colorant (D&C Yellow No. 5) | 0.02 |
| sodium chloride | 0.30 |

Preparation: Surfactant and water are blended until a homogeneous solution is obtained. The pH is adjusted to 6.0-6.5 with citric acid and the other components are added in the indicated sequence. The mixture is stirred until it is completely dissolved.

EXAMPLE 3

Preparation of a Perfumed Toilet Water

| Ingredients | (w/w) % |
| --- | --- |
| ethanol, 96% | 60 |
| d-limonene | 5 |
| cedrene | 1.5 |
| citronellol | 0.5 |
| savin | 0.5 |
| light stabilizer of formula (53) | 0.25 |
| antioxidant of formula (99) | 0.10 |
| S,S-EDDS | 0.01 |
| colorant (D&C Yellow No. 5) | 0.1 |
| water | ad. 100 |

Preparation: The components are thoroughly mixed in the indicated sequence at 50° C. A clear homogeneous solution is obtained.

Preparation of Formulations of Household Products

EXAMPLE 4

Preparation of a Green-Colored Glass Detergent

| Ingredients | (w/w) % |
| --- | --- |
| anionic/amphoteric surfactants (Lumorol RK) | 0.7 |
| butyl glycol | 5.0 |
| isopropanol | 20.0 |
| d-limonene | 4.00 |
| colorant (D&C Green No. 2) | 0.05 |
| light stabilizer of formula (54) | 0.10 |
| water, demin. | ad. 100 |

Preparation: The components are dissolved in the indicated sequence until a clear homogeneous mixture is obtained.

EXAMPLE 5

Preparation of a Floor Wax

| Ingredients | (w/w) % |
| --- | --- |
| wax mixture | 12 |
| white spirit | ad. 100 |
| d-limonene | 4.00 |
| light stabiliser of formula (55) | 0.10 |

Preparation: The components are stirred in the indicated sequence until a homogeneous mixture is obtained.

EXAMPLE 6

Preparation of a Lipstick, Non-Greasy

| Ingredients | (w/w) % |
| --- | --- |
| Carnauba wax | 2.5 |
| Beeswax, white | 20.0 |
| Ozekerite | 10.0 |
| Lanoline, anhydrous | 5.0 |
| Cetyl alcohol | 2.0 |
| Liquid paraffin | 3.0 |
| Isopropyl Myristate | 3.0 |
| Propylene glycol recinoleate | 4.0 |
| CI Pigment Red 4 | 9.0 |
| CI Pigment Blue 15 | 1.0 |
| Light stabilizer of formula (55) | 0.1 |
| Castor Oil | to 100 |

EXAMPLE 7

Preparation of a Lipstick, Transfer Resistant

| Ingredients | (w/w) % |
| --- | --- |
| Cyclomethicone | 41.50 |
| Isodecane | 10.00 |
| D&C Red No. 7 | 8.00 |
| Synthetic wax | 6.00 |
| Isostearyltrimethylpropane siloxysilicate | 5.00 |
| Cetylstearate/acetylated lanolin, 90:10 | 5.00 |
| Ceresin | 4.00 |
| Paraffin | 3.00 |
| Titanium dioxide | 2.00 |
| Methylparaben | 0.30 |
| Propylparaben | 0.10 |
| Antioxidant of formula (104) | 0.10 |
| light stabilizer of formula (54) | 0.10 |

EXAMPLE 8

Preparation of a Rouge (Powder)

| Ingredients | (w/w) % |
| --- | --- |
| Talc | 56 |
| Zinc Stearate | 15 |
| Rice starch | 15 |
| Iron Oxide Red | 12 |
| Perfume | q.s. |
| light stabilizer of formula (53) | 0.1 |

EXAMPLE 9

Preparation of a Foundation Cream

| Ingredients | (w/w) % |
| --- | --- |
| Titanium dioxide | 12.79 |
| Oleyl alcohol | 4.57 |
| Glyceryl stearate | 3.65 |
| Propylene glycol | 3.65 |
| Stearic acid | 1.83 |
| Magnesium aluminium silicate | 0.91 |
| Triethanolamine 99% | 0.91 |
| Iron Oxide Yellow | 0.64 |
| Iron Oxide Red | 0.32 |
| CI Pigment Brown 6 | 0.37 |
| Carboxymethyl cellulose | 0.10 |
| light stabilizer of formula (53) | 0.10 |
| Water | to 100 |

EXAMPLE 10

Preparation of an Eyeliner

| Ingredients | (w/w) % |
| --- | --- |
| Polysaccharide resin (Kama KM 13, Kama) | 8.00 |
| Iron Oxide Black | 6.50 |
| Carnauba wax | 1.00 |
| Triethanolamin, 99% | 1.00 |
| Hydrogenated polyisobutane | 1.00 |
| Hydrogenated polydecene | 1.00 |
| Sorbitan sesquioleate | 1.00 |
| Xanthum gum | 0.50 |
| Carboxymethyl cellulose | 0.40 |
| Magnesium aluminium silicate | 0.40 |
| Methyl paraben | 0.35 |
| Stearic acid | 2.50 |
| Lecithin | 0.20 |
| Imidazolidinyl urea | 0.10 |
| light stabilizer of formula (53) | 0.10 |
| Antioxidant of formula (100) | 0.05 |
| Water | to 100 |

EXAMPLE 11

Preparation of an Eyelash Makeup

| Ingredients | (w/w) % |
| --- | --- |
| Paraffin Wax | 10.00 |
| Starch | 5.00 |
| Polyethylene | 5.00 |
| Iron Oxide Black | 7.00 |
| Carbomer (Carbopol, B F Goodrich) | 0.50 |
| Hydroxyethylcellulose | 0.50 |
| Panthenol | 2.00 |
| Light stabilizer of formula (53) | 0.10 |
| Water | to 100 |

EXAMPLE 12

Preparation of a Nail Varnish

| Ingredients | (w/w) % |
| --- | --- |
| Poly(1-trimethylsilylpropylene) | 0.30 |
| Nitrocellulose | 12.00 |
| Alkyd resin | 10.00 |
| Dibutyl phthalate | 4.00 |
| Camphor | 2.00 |
| Butyl acetate | 49.50 |
| Toluene | 20.00 |
| Pigment Red 57.1 | 1.00 |
| Quaternary bentonite | 1.00 |
| Light stabilizer of formula (54) | 0.10 |
| Antioxidant of formula (103) | 0.10 |

What is claimed is:

1. A method for protecting body-care and household products wherein said body-care and household products are stored in a container, said container has a low absorption in the UV-A range and said body-care and household products are subject to photolytic degradation from UV light which comprises incorporating into said body care or household products from 50 to 1000 ppm of a benzotriazole of formula

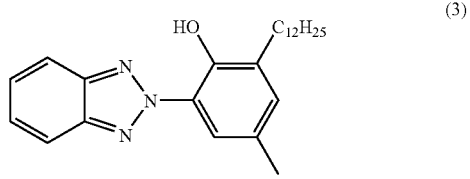

(3)

and optionally from 50 to 1000 ppm of a triazine compound of formula

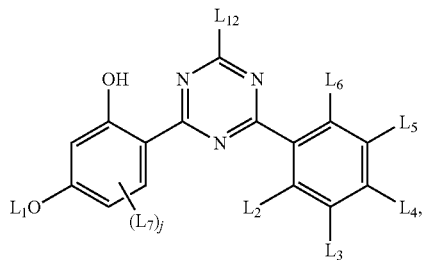
(2)

wherein

L$_1$ is C$_1$-C$_{22}$alkyl, C$_2$-C$_{22}$alkenyl or C$_5$-C$_7$cycloalkyl;

L$_2$ and L$_6$ are each independently of the other H, OH, halogen, C$_1$-C$_{22}$alkyl, halomethyl;

L$_3$, L$_5$ and L$_7$ are each independently of one another H, OH, OL$_1$, halogen, C$_1$-C$_{22}$alkyl, halomethyl;

L$_4$ is H, OH, OL$_1$, halogen, C$_1$-C$_{22}$alkyl, phenyl, halomethyl;

L$_{12}$ is C$_1$-C$_{22}$alkyl, phenyl C$_1$-C$_5$alkyl, C$_5$-C$_7$cycloalkyl, OL$_1$ or a group of formula

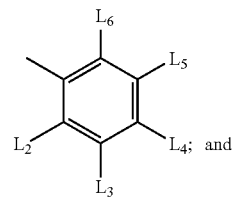; and j is 0, 1, 2 or 3 wherein said benzotriazole of formula (3) is completely dissolved in said body-care and said household products; and wherein said body-care and said household products comprise a pH range from 5.6 to 5.75 or a pH range from 6.0 to 6.5.

2. The method according to claim 1, wherein said body care or household product further contains a fragrance or odoriferous substance.

* * * * *